(12) United States Patent  (10) Patent No.: US 8,167,924 B2
Rosenbaum  (45) Date of Patent: May 1, 2012

(54) THERAPEUTIC GARMENT

(76) Inventor: Molly M. Rosenbaum, Scottsdale, AZ (US)

( * ) Notice: Subject to any disclaimer, the term of this patent is extended or adjusted under 35 U.S.C. 154(b) by 395 days.

(21) Appl. No.: 12/468,772

(22) Filed: May 19, 2009

(65) Prior Publication Data

US 2010/0298914 A1   Nov. 25, 2010

(51) Int. Cl.
*A61F 7/00* (2006.01)
(52) U.S. Cl. .......... 607/108; 607/112; 607/114; 450/86; 450/89
(58) Field of Classification Search .................... 450/86, 450/89; 607/108, 112, 114
See application file for complete search history.

(56) References Cited

U.S. PATENT DOCUMENTS

| | | | | |
|---|---|---|---|---|
| 1,804,855 A * | 5/1931 | Bollwine | ......................... | 450/83 |
| 2,298,361 A | 11/1941 | Freund | | |
| 4,335,728 A * | 6/1982 | Fildan | ............................. | 450/36 |
| 4,550,734 A * | 11/1985 | Porco | ............................. | 450/36 |
| 4,633,876 A * | 1/1987 | Scullin | ............................. | 450/36 |
| 4,816,005 A * | 3/1989 | Braaten | ........................... | 450/58 |
| 5,022,887 A * | 6/1991 | Lawson | ........................... | 450/54 |
| 5,235,974 A | 8/1993 | Miller | | |
| 5,304,215 A | 4/1994 | MacWhinnie et al. | | |
| 5,427,563 A | 6/1995 | Manning | | |
| 5,507,794 A | 4/1996 | Allen | | |
| 5,667,422 A * | 9/1997 | Erwin | ............................. | 450/30 |
| 5,679,052 A | 10/1997 | Rucki | | |
| 5,839,942 A | 11/1998 | Miller | | |
| 6,394,879 B1 * | 5/2002 | Paige | ............................. | 450/38 |
| 6,464,717 B1 | 10/2002 | Smith et al. | | |
| 7,081,034 B1 * | 7/2006 | Zoellner | ........................ | 450/54 |
| D529,259 S | 10/2006 | Faagau | | |
| 7,275,977 B1 | 10/2007 | Rhodes | | |
| 7,309,275 B1 | 12/2007 | Morales | | |
| 2001/0037076 A1 * | 11/2001 | Shelton | ............................ | 602/7 |
| 2005/0085162 A1 * | 4/2005 | Ott | ................................ | 450/150 |
| 2006/0048547 A1 * | 3/2006 | Duckham et al. | ............... | 66/176 |
| 2006/0154566 A1 | 7/2006 | Nunez et al. | | |

* cited by examiner

*Primary Examiner* — Roy Gibson
*Assistant Examiner* — Kaitlyn Smith
(74) *Attorney, Agent, or Firm* — Parsons & Goltry; Michael W. Goltry; Robert A. Parsons

(57) ABSTRACT

A therapeutic garment includes a brassiere having opposed first and second shoulder straps formed with opposed first and second breast-receiving cups, respectively, each having an outer surface. A reusable gel pack for heat or cold therapy is suspended from the first and second shoulder straps, extends downwardly from the first and second shoulder straps to the first and second breast-receiving cups, and overlies and extends across the outer surfaces of the first and second breast-receiving cups to provide heat or cold therapy to the first and second breast-receiving cups at the outer surface of each of the first and second breast-receiving cups.

8 Claims, 7 Drawing Sheets

THERAPEUTIC GARMENT

FIELD OF THE INVENTION

The present invention relates undergarments and, more particularly, to women's undergarments and especially brassieres and to therapeutic brassieres.

BACKGROUND OF THE INVENTION

Women who are breastfeeding or recovering from breast surgery commonly experience breast swelling and pain, which is effectively treated through the application of hot and cold therapy to the breasts. To assist women in applying hot and cold therapy to the breasts, skilled artisans have developed numerous examples of brassieres with breast-receiving cups formed with pockets to receive hot/cold packs. When such brassieres are worn, the hot/cold packs applied to the breast-receiving cups are desirably positioned to apply hot or cold therapy to the breasts. The problem with such brassieres and like or similar garments is that the cups bear the weight of the hot/cold packs. Because the breasts that have undergone surgical treatment and the breasts of breastfeeding women are often tender and highly sensitive to tactile forces, the weight imparted to the breast receiving cups by the hot/and cold packs formed in the breast-receiving cups is painful and uncomfortable, thereby necessitating improvements in the art.

SUMMARY OF THE INVENTION

According to the principle of the invention, a therapeutic garment includes a brassiere having opposed first and second shoulder straps formed with opposed first and second breast-receiving cups, respectively, each having an outer surface. A reusable gel pack for heat or cold therapy is suspended from the first and second shoulder straps, extends downwardly from the first and second shoulder straps to the first and second breast-receiving cups, and overlies and extends across the outer surfaces of the first and second breast-receiving cups to provide heat or cold therapy to the first and second breast-receiving cups at the outer surface of each of the first and second breast-receiving cups. An inverted pocket is formed in the first shoulder strap, and the reusable gel pack is suspended from the first shoulder strap from within the inverted pocket formed in the first shoulder strap. An inverted pocket is also formed in the second shoulder strap, and the reusable gel pack is suspended from the second shoulder strap from within the inverted pocket formed in the second shoulder strap.

According to the principle of the invention, a therapeutic garment includes a brassiere having opposed first and second shoulder straps formed with opposed first and second breast-receiving cups, respectively, each having an outer surface. A reusable gel pack for heat or cold therapy is also provided. First and second engagement elements are formed in the first and second shoulder straps, respectively. First and second complemental engagement elements are formed in the reusable gel pack, and are detachably secured to the first and second engagement elements, respectively, detachably suspending the reusable gel pack from the first and second shoulder straps. The reusable gel pack extends downwardly from the first and second shoulder straps to the first and second breast-receiving cups, and overlies and extends across the outer surfaces of the first and second breast-receiving cups to provide heat or cold therapy to the first and second breast-receiving cups at the outer surface of each of the first and second breast-receiving cups. The first engagement element is one of a male engagement element and a female engagement element, and the first complemental engagement element is the other of the male engagement element and the female engagement element. The second engagement element is one of a male engagement element and a female engagement element, and the second complemental engagement element is the other of the male engagement element and the female engagement element. An inverted pocket is formed in the first shoulder strap, and the first engagement element is formed in the inverted pocket formed in the first shoulder strap. The first engagement element is elastically coupled to the first shoulder strap for movement between a first position in the inverted pocket formed in the first shoulder strap and a second position extending outwardly with respect to the inverted pocket formed in the first shoulder strap toward the first breast-receiving cup. An inverted pocket is also formed in the second shoulder strap, and the second engagement element is formed in the inverted pocket formed in the second shoulder strap. The second engagement element is elastically coupled to the second shoulder strap for movement between a second position in the inverted pocket formed in the second shoulder strap and a second position extending outwardly with respect to the inverted pocket formed in the second shoulder strap toward the second breast-receiving cup.

According to the principle of the invention, a therapeutic garment includes a brassiere having opposed first and second shoulder straps formed with opposed first and second breast-receiving cups, respectively, each having an outer surface. A reusable gel pack for heat or cold therapy is formed with opposed first and second connector straps. First and second engagement elements are formed in the first and second shoulder straps, respectively. First and second complemental engagement elements are formed in first and second connector straps, respectively, which are detachably secured to the first and second engagement elements, respectively, formed in the first and second shoulder straps detachably suspending the reusable gel pack from the first and second shoulder straps. The first and second connector straps extend downwardly along the first and second shoulder straps, respectively, to the reusable gel pack overlying and extending across the outer surfaces of the first and second breast-receiving cups to provide heat or cold therapy to the first and second breast-receiving cups at the outer surface of each of the first and second breast-receiving cups. The first engagement element is one of a male engagement element and a female engagement element, and the first complemental engagement element is the other of the male engagement element and the female engagement element. The second engagement element is one of a male engagement element and a female engagement element, and the second complemental engagement element is the other of the male engagement element and the female engagement element. An inverted pocket is formed in the first shoulder strap, and the first engagement element is formed in the inverted pocket formed in the first shoulder strap. The first engagement element is elastically coupled to the first shoulder strap for movement between a first position in the inverted pocket formed in the first shoulder strap and a second position extending outwardly with respect to the inverted pocket formed in the first shoulder strap toward the first breast-receiving cup. An inverted pocket is also formed in the second shoulder strap, and the second engagement element is formed in the inverted pocket formed in the second shoulder strap. The second engagement element is elastically coupled to the second shoulder strap for movement between a second position in the inverted pocket formed in the second shoulder strap and a second position extending outwardly with respect to the inverted pocket formed in the second shoulder strap toward the second breast-receiving cup.

BRIEF DESCRIPTION OF THE DRAWINGS

Referring to the drawings.

DETAILED DESCRIPTION OF PREFERRED EMBODIMENTS

Figure 1:
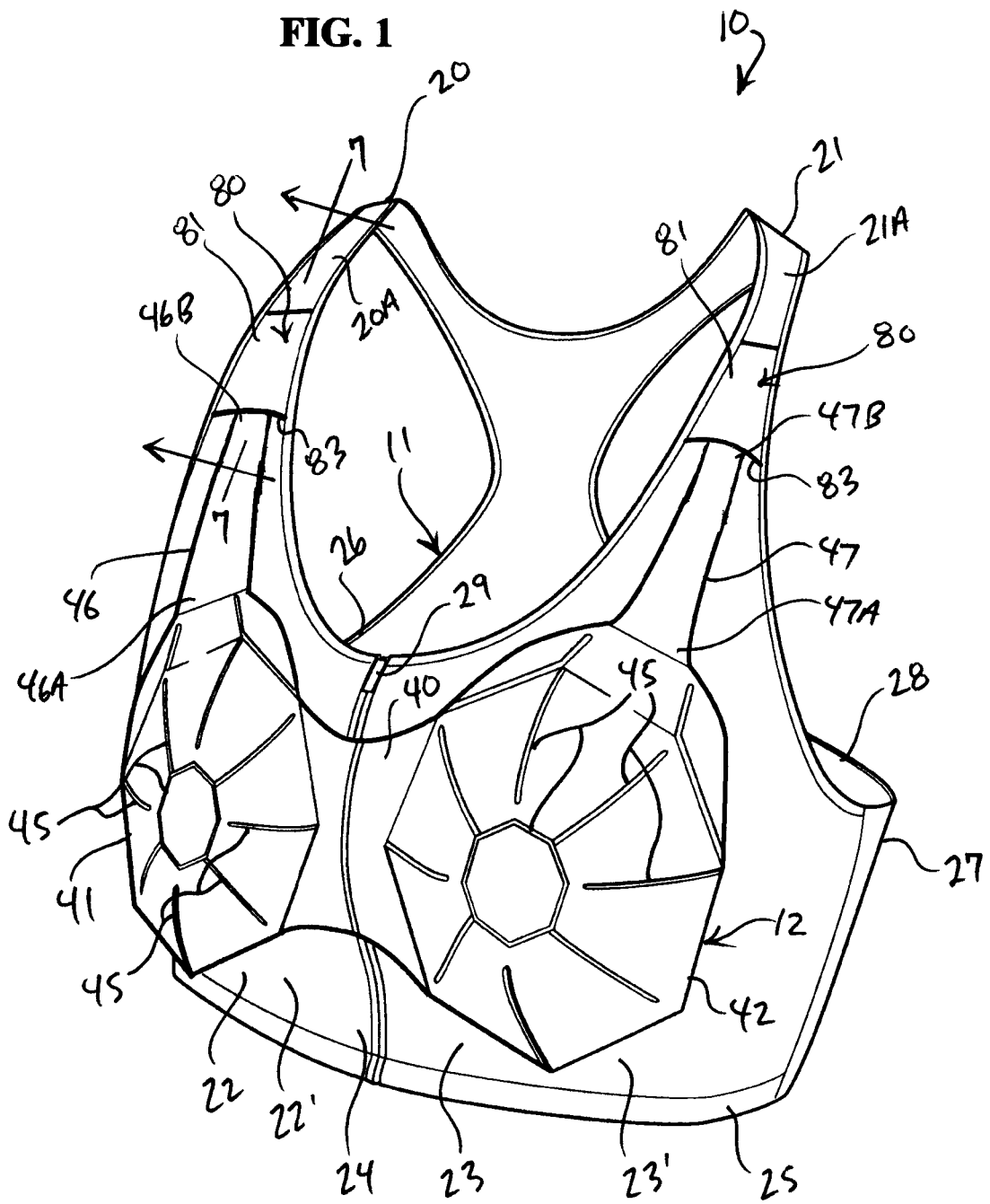
FIG. 1 is a perspective view of therapeutic garment including a brassiere having shoulder straps formed with opposed breast-receiving cups, and a reusable gel pack for heat or cold therapy suspended from straps of the brassiere to overly extend across outer surfaces of breast-receiving cups.
Figure 8:
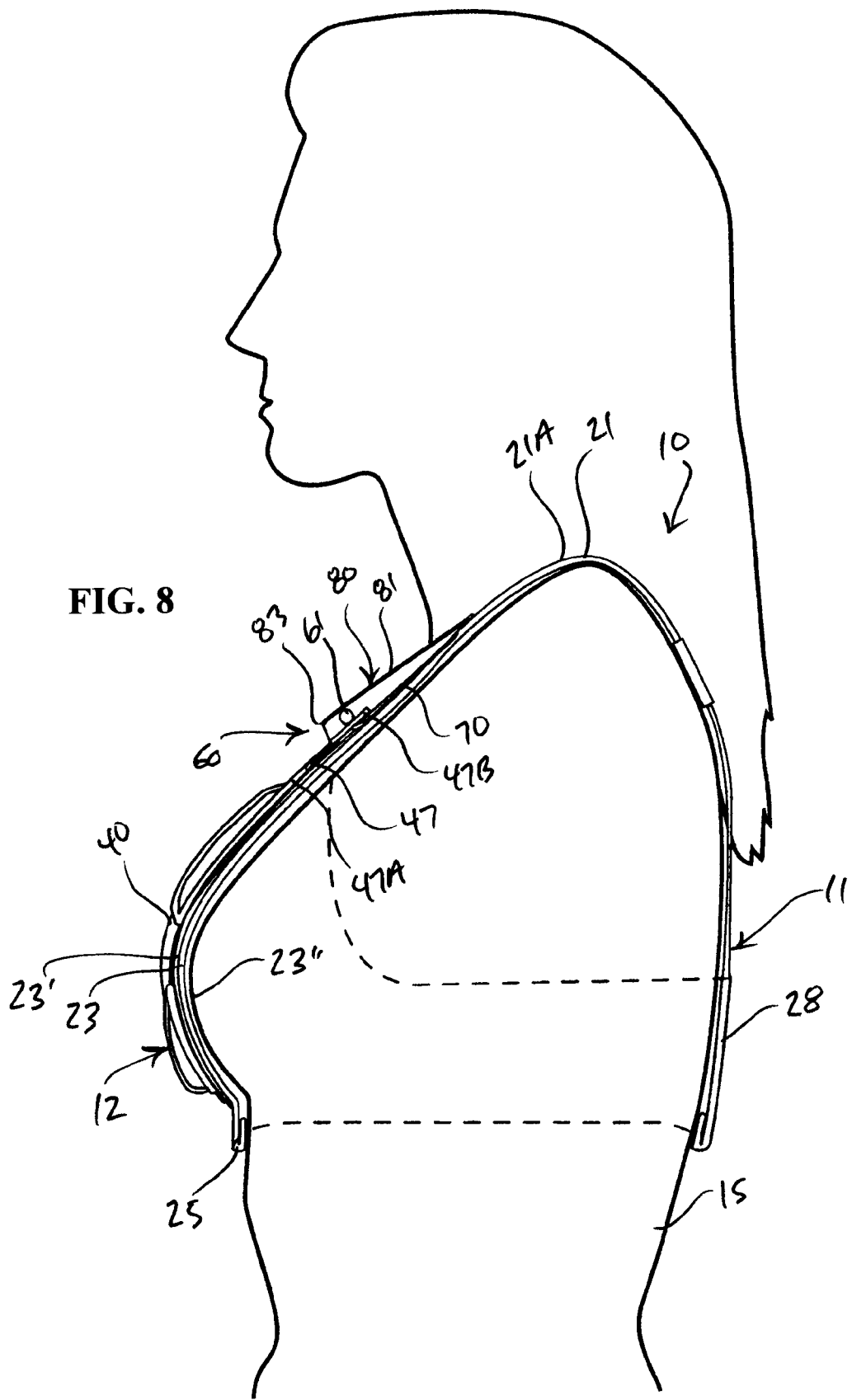
FIG. 8 is a partially schematic side elevation view illustrating the therapeutic garment as it would appear in use.

Turning now to the drawings, in which like reference characters indicate corresponding elements throughout the several views, attention is first directed to FIG. 1 is a perspective view of therapeutic garment 10 including a brassiere 11 and a reusable gel pack 12 for heat and cold therapy. Referencing FIGS. 1 and 2, brassiere 11 is a foundation garment for a woman consisting of shoulder straps 20 and 21 formed with two breast-receiving cups 22 and 23, a center panel 24 between cups 22 and 23, an underbust band 25 underlying cups 22 and 23, sides 26 and 27, and a back 28 opposing center panel 24. Shoulder straps 20 and 21 are substantially equal in length and size and shape, and extend cups 22 and 23, respectively, and back 28. Cups 23 and 24 have inner breast-receiving surfaces, and an opposing outer surface 22' and 23', respectively. Outer surfaces 22' and 23' are each generally convex, and the opposed inner breast-receiving surfaces of cups 22 and 23 are each generally concave so as to receive a breast as with conventional brassieres. FIG. 8 is a partially schematic side elevation view illustrating brassiere 11 as it would appear in use and worn by a female user 15 providing breast coverage and support. As a matter of illustration and reference, the profile of cup 23 is shown in FIG. 8 showing outer surface 23', which is generally convex, and opposed inner breast-receiving surface 23", which is generally concave so as to receive a breast, and the inner breast-receiving surface of cup 22 is similarly arranged.

Center panel 24 is formed with a closure 29 for permitting brassiere 11 to be easily installed in place and removed, being exemplary of a front-closure style of brassiere, which is common with athletic brassieres. In the present example, closure 29 is a zipper. Other forms of closures can be used, if desired. If desired, the back of brassiere 11 may be formed with a clasp or closure assembly for permitting brassiere 10 to be easily installed in place and removed, being exemplary of a back-closure style of brassiere. Brassiere 11 is fashioned of cotton, polyester, silk, or other material or combination of materials as with conventional brassieres.

With the exception of the improvements incorporated into brassiere 11 to form therapeutic garment 10, brassiere 11 is a close-fitting garment generally representative of a conventional brassiere of the type which is adapted to be worn by a woman for providing breast coverage and support. Various details of brassiere 11 not herein specifically discussed will readily occur to those skilled in the art and will not be further discussed except to the extent necessary to make a full and complete disclosure of the invention. Furthermore, bra types are quite varied, depending on style, function, and materials. Accordingly, brassiere 11 can be fashioned of any suitable style as may be desired, in which such styles can include a front-closure style, a back-closure style, a strapless style, a convertible style, a push-up style, a demi-bra style, a full-cup style, three-quarters cup style, a half-cup style, a longline style, an underwire style, a padded style, a triangle style, a soft-cup style, a shelf-bra style, a T-shirt style, etc.

In therapeutic garment 10 illustrated in FIG. 1, gel pack 12 is suspended from straps 20 and 21, extends downwardly from shoulder straps 20 and 21 to cups 22 and 23, and overlies and extends across outer surfaces 22' and 23' of cups 22 and 23, respectively, to provide thermal therapy, such heat therapy when gel pack 12 is heated, or cold therapy when gel pack 12 is chilled, to cups 22 and 23 at outer surfaces 22' and 23', respectively. The thermal therapy, i.e. heat or cold, is imparted to cups 22 and 23 from gel pack 12, and is transmitted through cups 22 and 23 to breasts received in cups when brassiere 11 is worn by a female in the normal manner. In other words, when brassiere 11 is worn in the normal manner by a female user 15 providing breast coverage and support with cups 22 and 23 applied over the opposed breasts of female 15, gel pack 12 attached to brassiere 11, as illustrated in FIGS. 1 and 8, forming therapeutic garment 10 apply the thermal therapy to the opposed breasts of female 15 through the opposed cups 22 and 23, in accordance with the principle of the invention, when such thermal therapy is required, such as after breast reduction surgery, breast enlargement therapy, or other breast procedure requiring or benefiting from post-procedure thermal therapy.

Gel pack 12 is suspended from straps 20 and 21 at an intermediate location of straps 20 and 21 between back 28 of brassiere 11 and cups 22 and 23. This is important because the weight of gel pack 12 is born by straps 20 and 21, and not by cups 22 and 23, which is more comfortable, and which does not add weight to cups 22 and 23 which could otherwise draw cups 22 and 23 away from the breast fitted therein or cause breast pain or discomfort.

Figure 3:
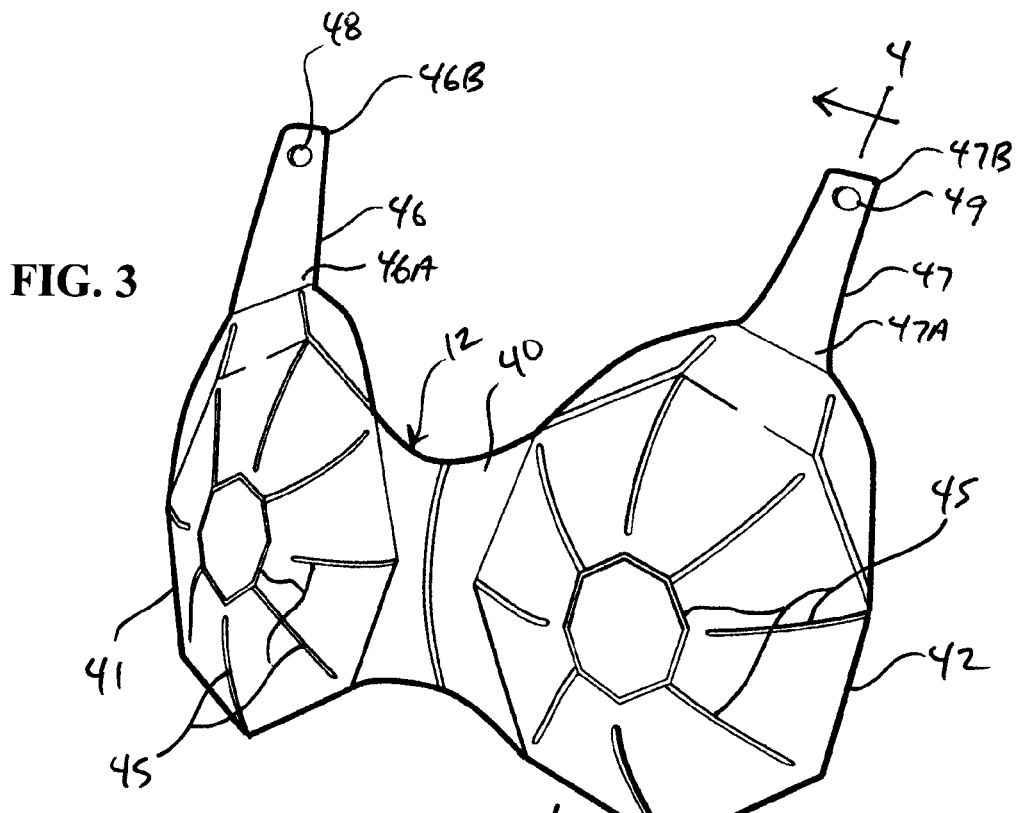
FIG. 3 is a perspective view of the gel pack of FIG. 1.
Figure 4:
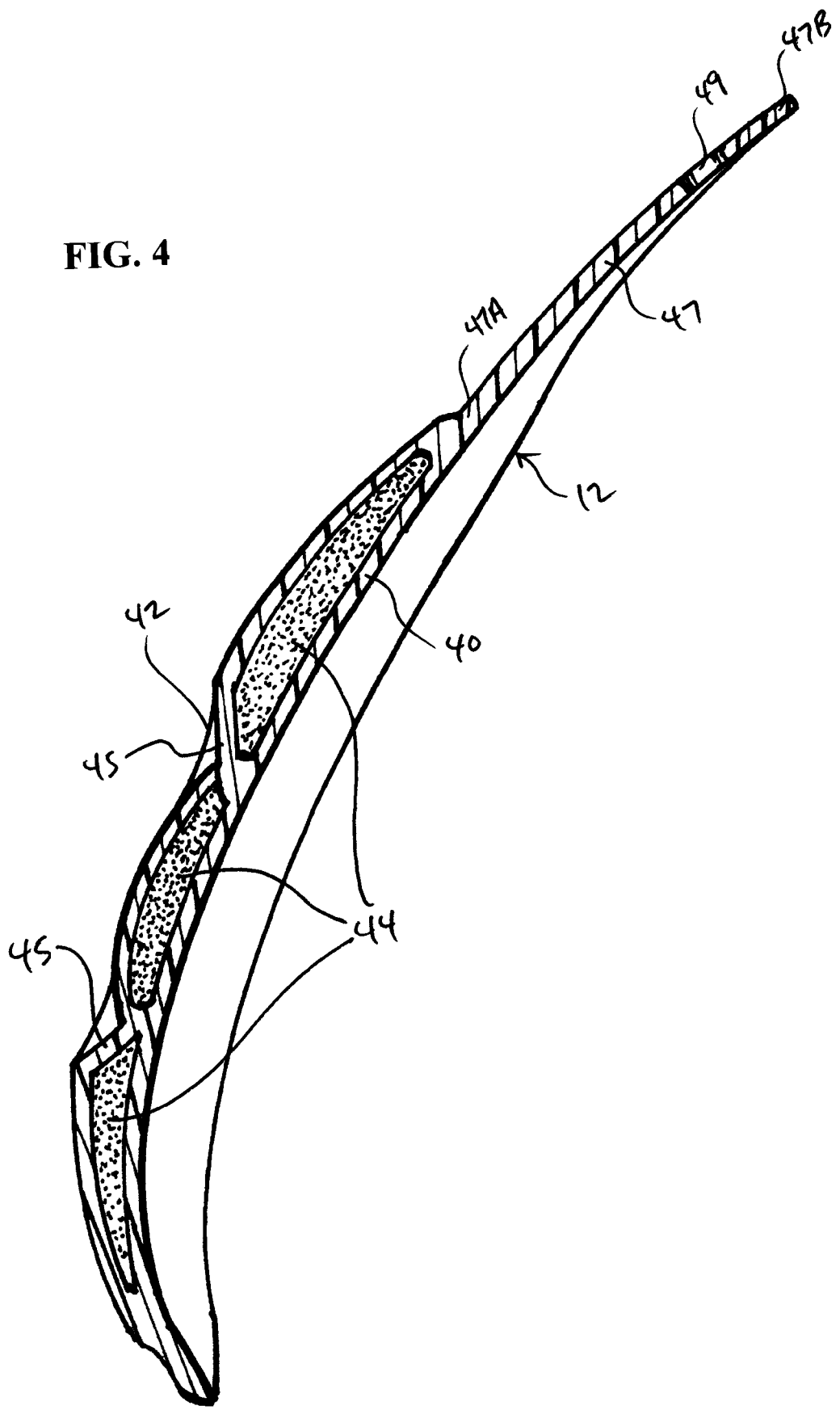
FIG. 4 is a sectional view taken along line 4-4 of FIG. 3.

Referencing FIG. 3, gel pack 12 consists of flexible sac or bladder 40 of a viscous refrigerant material, such as a refrigerant gel, a refrigerant liquid, or the like, which may be chilled, such as by placing gel pack 12 in a refrigerator until chilled, to provide cold therapy, or heated, such as by placing gel pack 12 in hot water or running hot water of gel pack 12 until heated, to provide heat therapy as may be desired. Bladder 40 is broad and substantially flat, is filled with refrigerant gel or liquid, and is formed a pair of opposed, equally-sized and shaped sections 41 and 42. Sections 41 and 42 are formed with baffles 45, which keep the viscous refrigerant material substantially evenly disbursed throughout bladder 40 and in sections 41 and 42. FIG. 4 is a sectional view taken along line 4-4 of FIG. 3, and illustrates viscous refrigerant material 44 formed in section 42 of bladder 40, and baffles 45 formed in section 42 to keep viscous refrigerant material 44 substantially evenly disbursed in section 42. Section 41 is similarly arranged.

Bladder 40 is formed with opposed connector straps 46 and 47, which are used to attach and suspend gel pack 12 to brassiere 11 to form therapeutic garment 10. Strap 46 is formed with section 41, and strap 47 is formed with section 42. Straps 46 and 47 are substantially equal in size, shape, and length. Strap 46 has an inner end 46A formed with section 41, and extends upwardly/outwardly therefrom to an opposed outer end 46B. Strap 47 has an inner end 47A formed with section 42, and extends upwardly/outwardly therefrom to an opposed outer end 47B. Ends 47A and 47B of straps 46 and 47 are preferably affixed to sections 41 and 42, respectively, such as by integral formation, heat bonding, sewing, or the like. As such, straps 46 and 47 are not detachable or otherwise not intended to be detached from sections 41 and 42, respectively. In other embodiments, ends 46A and 47A of straps 46 and 47 may be detachably secured to sections 41 and 42 with suitable fasteners, such as mutual snap fasteners, hook-and-loop fasteners, button fasteners, etc.

According to the invention, an engagement assembly is formed between outer end 46B of strap 46 and strap 20 of brassiere 11, and an engagement assembly is formed between outer end 47B of strap 47 and strap 21 of brassiere 11. The respective engagement assemblies between straps 46 and 47 of gel pack 12 and straps 20 and 21 of brassiere 11 are identical and detachably attach and suspend gel pack 12 to straps 20 and 21 of brassiere 11. As such, only the details of the engagement assembly formed between strap 46 of gel pack 12 and strap 20 of brassiere 11 will be discussed, with the understanding that the ensuing discussion applies equally to the engagement assembly between strap 47 of gel pack 12 and strap 21 of brassiere 11.

Figure 5:
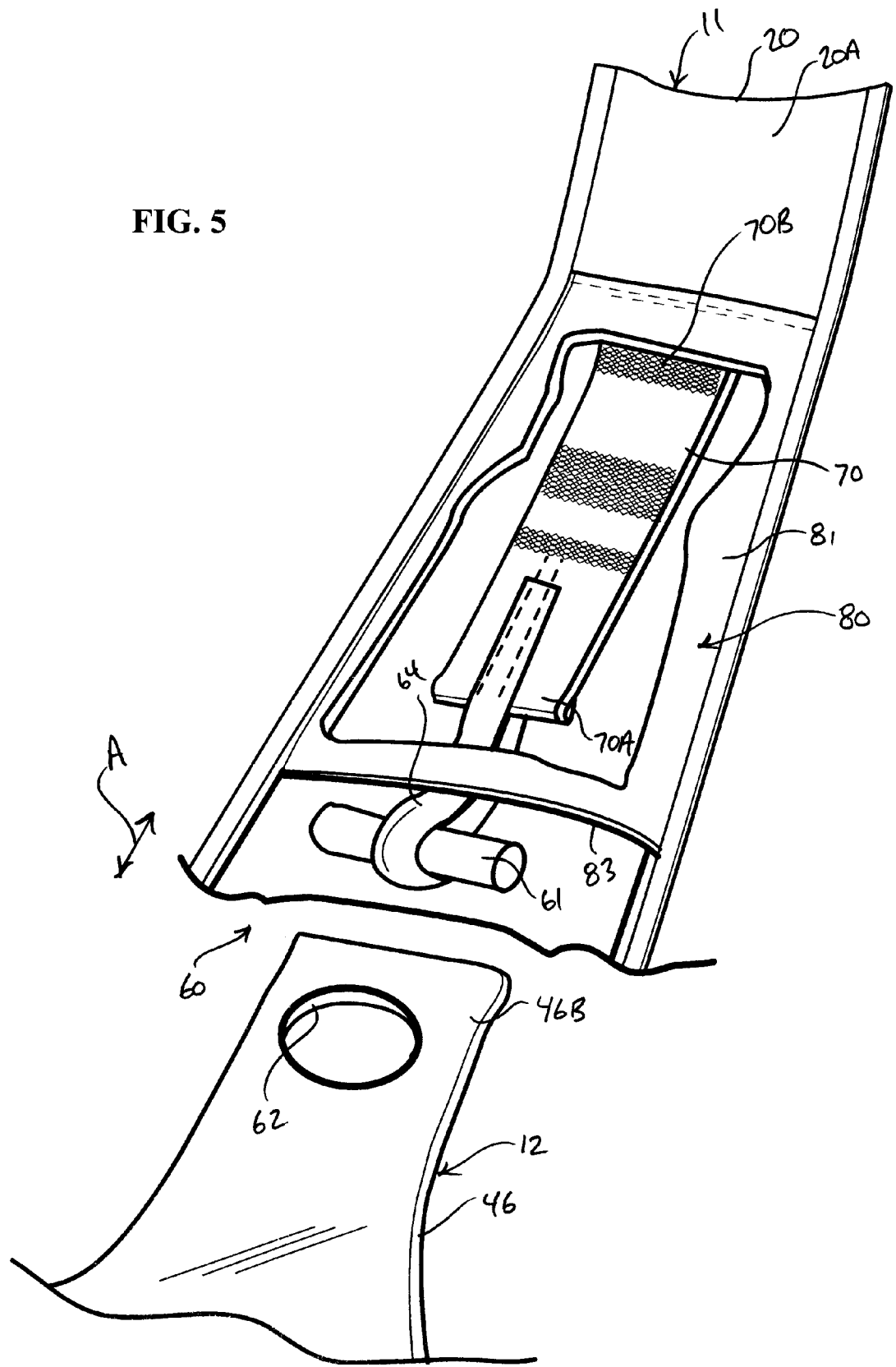
FIG. 5 is a fragmented perspective view of the therapeutic garment of FIG. 1 illustrating an engagement assembly formed between the brassiere and the gel pack including an element thereof formed in one of the straps of the brassiere and a complemental engagement element formed in a connector strap of the gel pack, and the engagement element shown as it would appear disengaged with respect to the complemental engagement element.

In FIG. 5 there is illustrated an engagement assembly 60 formed between brassiere 11 and gel pack 12 including an element thereof formed in strap 20 of brassiere 11 and a complemental engagement element formed in outer end 46B of strap 46 of gel pack 12. The engagement element formed in strap 20 is formed at an intermediate location along the length of strap between back 28 of brassiere 11 and cup 22. In the present embodiment, engagement assembly 60 is a bullet jess assembly, in which the engagement element formed in strap 20 of brassiere 11 is a T-portion 61 of the bullet jess assembly formed in strap 20 between cup 22 and back 28 of brassiere 11 denoted in FIGS. 1 and 2, and the complemental engagement element formed in outer end 46B of strap 46 of gel pack 12 is a corresponding grommet 62. T-portion 61 is located along outer surface 20A of strap 21 that faces outwardly with respect to a user wearing brassiere 11 and that is continuous or contiguous with outer surface 22' of cup 22 denoted in FIGS. 1 and 2. T-portion 61 is formed conventionally in a bullet jess strap 64 that is, in turn, affixed, such as by sewing or with a suitable adhesive, to an outer end 70A of an elastic strip 70, the opposing inner end 70A of which is affixed, such as by sewing or with a suitable adhesive, to strap 20. Bullet jess strap 64 and elastic strip 70 extend along outer surface 20A of strap 20 of brassiere 11.

Figure 6:
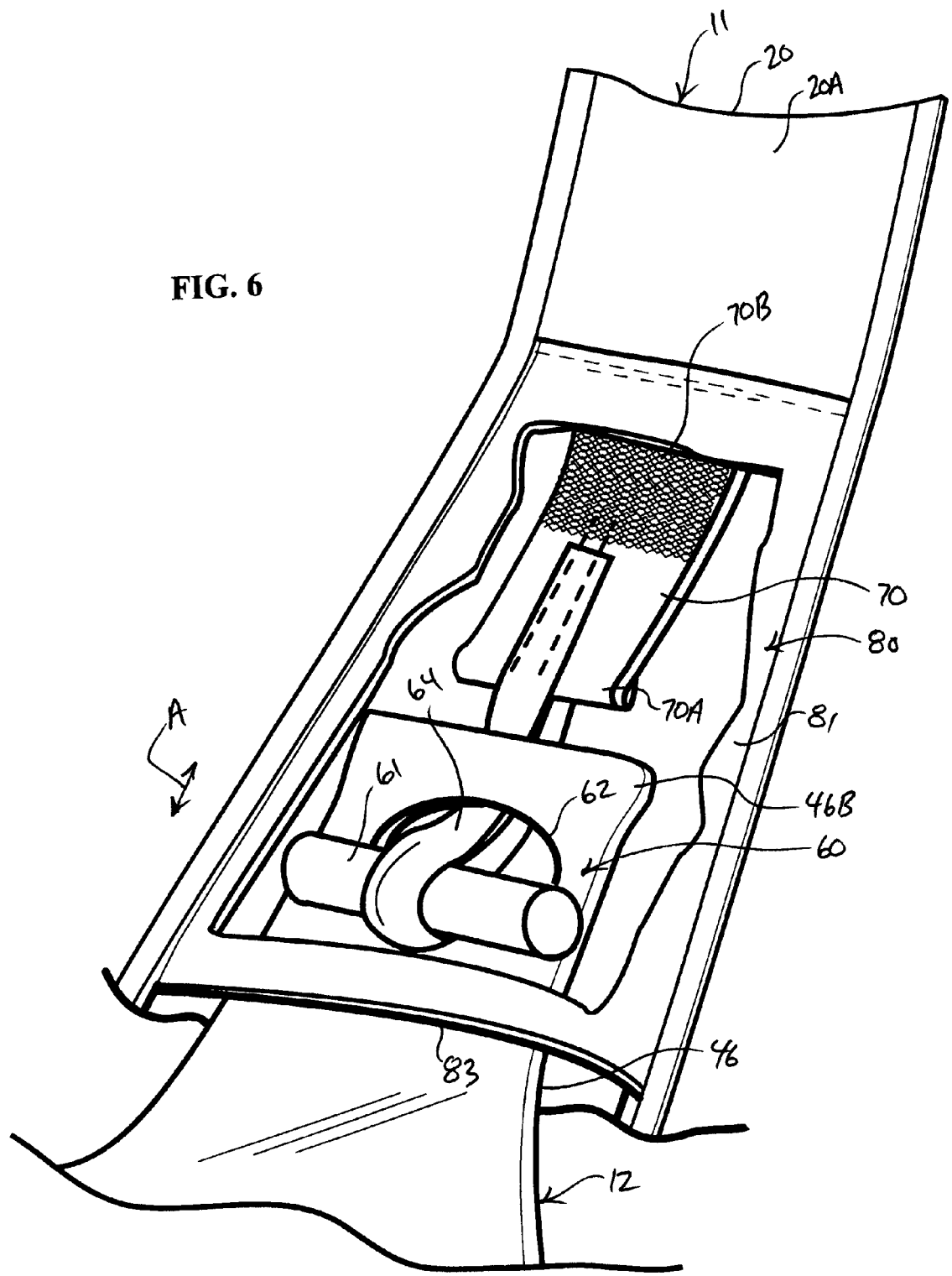
FIG. 6 is a view very similar to that of FIG. 5 illustrating the engagement element shown at it would appear engaged with respect to the complemental engagement element.
Figure 7:
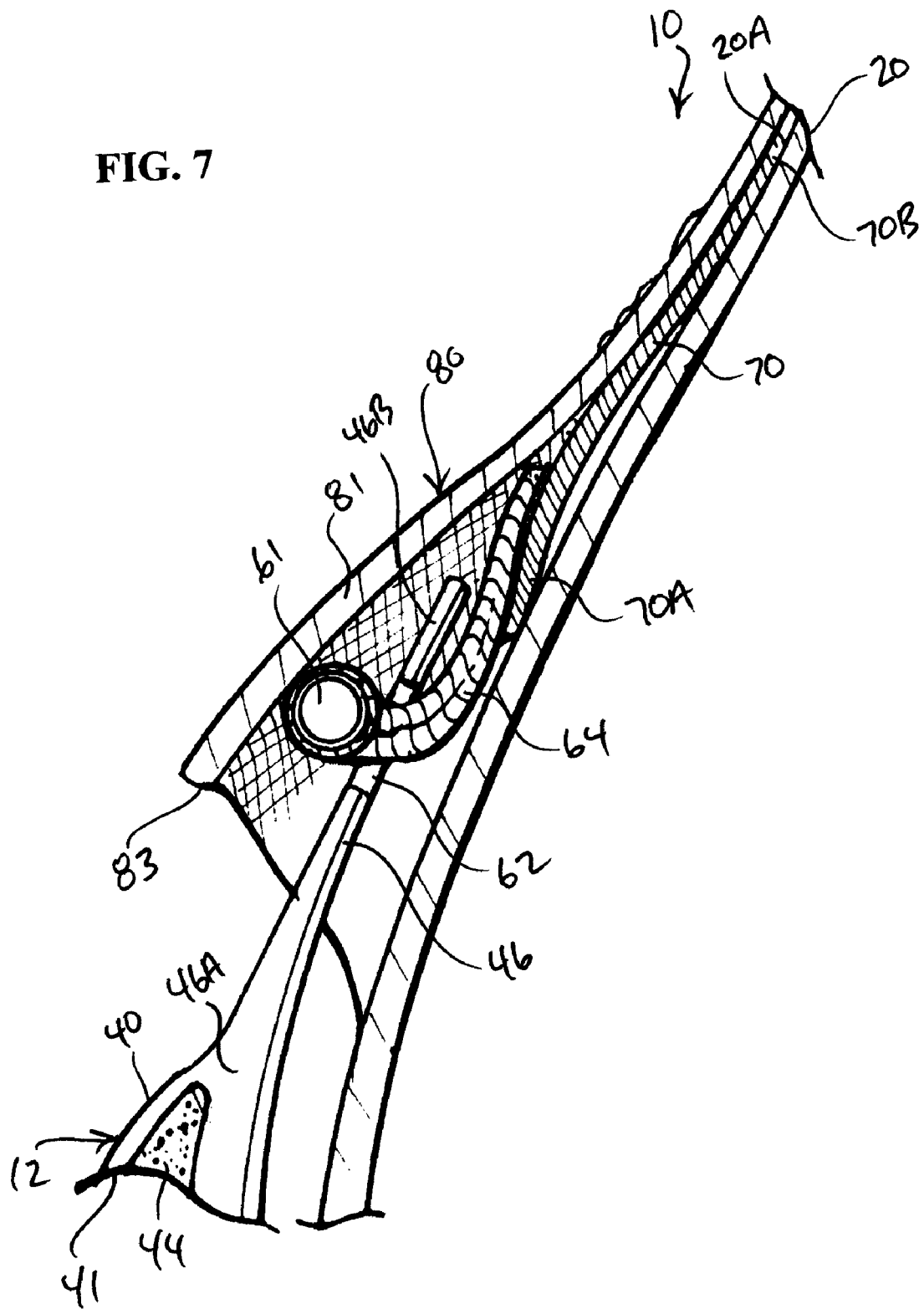
FIG. 7 is a sectional view taken along line 7-7 of FIG. 1.

FIG. 5 illustrates the engagement element in strap 20 formed by T-portion 61 as it would appear disengaged with respect to the complemental engagement element in strap 46 of gel pack 12 formed by grommet 62. To attach T-portion 61 to grommet 62 to detachably secure strap 20 of brassiere 11 to strap 46 of gel pack 12, one need only direct T-portion 61 into and through grommet 62 as shown in FIGS. 6 and 7. By so attaching both straps 46 and 47 of gel pack 12 to straps 20 and 21, respectively, with the respective engagement assemblies 60, gel pack 12 is detachably engaged to and suspended from straps 20 and 21 as in FIG. 1, such that gel pack 12 is suspended from straps 20 and 21, extends downwardly from shoulder straps 20 and 21 to cups 22 and 23, and overlies and extends across outer surfaces 22' and 23' of cups 22 and 23, respectively, to provide thermal therapy, such heat therapy when gel pack 12 is heated, or cold therapy when gel pack 12 is chilled, to cups 22 and 23 at outer surfaces 22' and 23', respectively, to thereby impart the thermal therapy to the breasts of a user received in cups 22 and 23. To detach T-portion 61 from grommet 62 to detach strap 46 of gel pack 12 from strap 20 of brassiere 11 to thereby detach gel pack 12 from strap 20 of brassiere 11, the foregoing operation for attaching T-portion 61 to grommet 62 need only be reversed.

It is to be emphasized that the engagement elements formed in straps 20 and 21 are located at an intermediate location along straps 20 and 21 between cups 22 and 23, respectively, and back 28 of brassiere 11. As such, when the complemental engagement elements of the respectively engagement assemblies 60 are attached to detachably secure gel pack 12 to straps 20 and 21, the weight of gel pack 12 is born by straps 20 and 21, and not by cups 22 and 22, which is more comfortable, and which does not add weight to cups 22 and 23 which could otherwise draw cups 22 and 23 away from the breast fitted therein or cause breast pain or discomfort.

Figure 2:
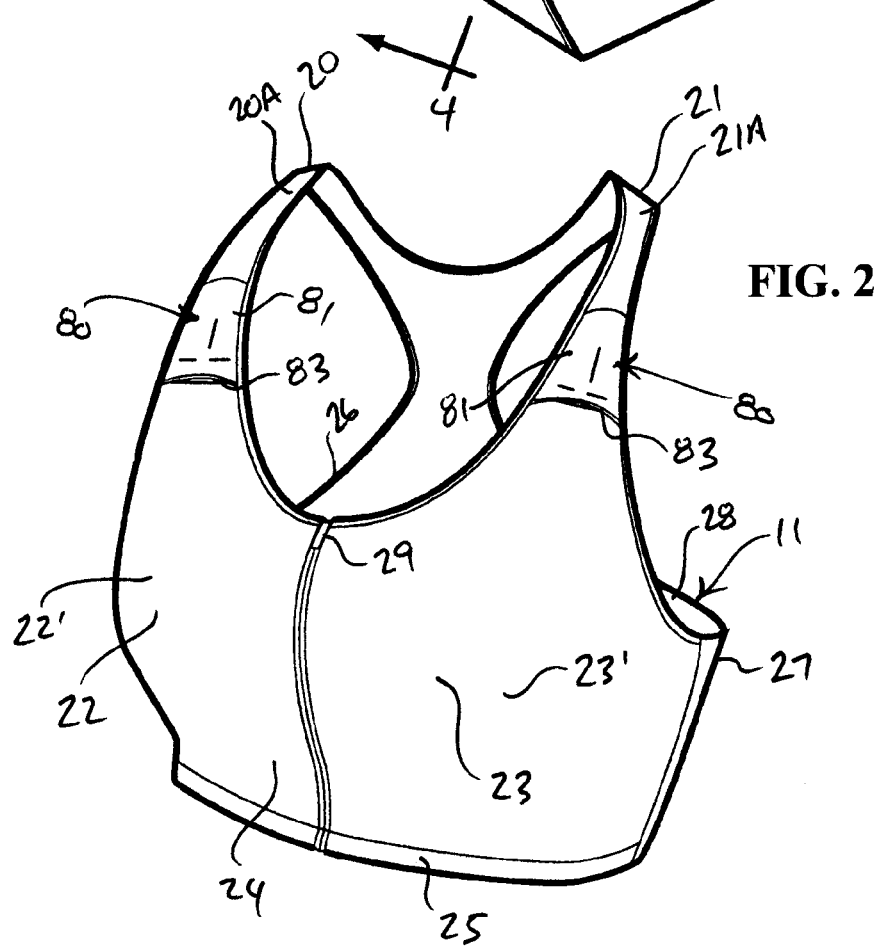
FIG. 2 is a perspective view of the brassiere of FIG. 1.

Looking back to FIGS. 1, 2, and 5, an inverted pouch or pocket 80 is formed in outer surface 20Aa of strap 20. Pouch or pocket 80 is formed in strap 20 at an intermediate location between back 28 of brassiere 11 and cup 22 as illustrated in FIGS. 1 and 2, and contains the engagement element of engagement assembly 60 illustrated in FIGS. 5 and 6. Pouch or pocket 80 consists of a shaped piece of material 81 or fabric that is attached, such as by sewing, to outside of strap 20 along outer surface 20A of strap 20 forming pouch or pocket 80 having an open end 83 directed downwardly from strap 20 toward cup 22 as illustrated best in FIGS. 1 and 2.

In FIGS. 5 and 6, a central portion of material 81 is broken away for illustrative purposes to show engagement element of engagement assembly 60 formed by T-portion 61, bullet jess strap 64, and elastic strip 70, formed in pocket 80. Elastic strip 70 is flat and is formed of any suitable and conventional and well-known flat elastic band material, and is stretchable between a shortened, relaxed state illustrated in FIGS. 6 and 7 to locate T-portion in pocket 80, and a lengthened, stretched state illustrated in FIG. 5 to locate T-portion 61 out of pocket 80 through open end 83. The flat shape of elastic strip 70 eliminates any possibility of shoulder discomfort at strap 20 when brassiere 11 is worn in the normal manner. Elastic band 70 couples T-portion 61 to strap 20 of brassiere 11, and provides an elastic coupling between strap 20 and the engagement element of engagement assembly 60 formed by T-portion 61 as indicated by the double arrowed line A in FIGS. 5 and 6 between a first or retracted position of T-portion 61 in pocket 80 away from cup 22 illustrated in FIG. 6 and a second or extended position of T-portion 61 extending outwardly through open end 83 of pocket 80 and downwardly toward cup 22 as illustrated in FIG. 5 (cup 22 not shown in FIG. 5).

In the shortened, relaxed state of elastic strip 70 when elastic strap 70 is under no stretching influence as illustrated in FIGS. 6 and 7, T-portion 61 is located in pocket 80 in a secure stored position and is concealed from view and protected, which allows brassiere 11 to be worn in the normal manner. In the lengthened, stretched state of elastic strip 70 illustrated in FIG. 5, T-portion 61 extends outwardly from open end 83 of pocket 80 in preparation for attachment to grommet 62.

To move elastic strip 70 between its relaxed and stretched positions, one need only reach into pocket 80 through open end 83, take up T-portion 61, such as with a couple fingers, and pull T-portion 61 to stretch elastic strip 70 to pull T-portion 61 out of pocket 80 through open end 83 illustrated in FIG. 5. At this point, T-portion 61 may be conveniently attached to grommet 62 formed in outer end 46A of strap 46 of gel pack 12 to attach and suspend gel pack 12 to strap 20, after which T-portion 61 may be released. After releasing T-portion 61 attached to grommet 62, elastic strip 70 constricts to its relaxed and shortened state to draw T-portion 61 and outer end 46A of strap 46 of gel pack 12 into pocket 80 illustrated in FIGS. 6 and 7, which conceals engagement assembly 60 between strap 46 of gel pack 12 and strap 20 of brassiere 11 and prevents engagement assembly 60 from inadvertently detaching to cause gel pack 12 to inadvertently fall away from brassiere 11 during use.

After use of gel pack 12 in conjunction with brassiere 11 is no longer needed, one need only pull downwardly against gel pack 12 to stretch elastic strip 70 to pull T-portion 61 out of pocket 80 through open end 83 illustrated in FIG. 5. At this point, T-portion 61 may be conveniently detached from grommet 62 formed in outer end 46A of strap 46 of gel pack 12 to detach gel pack 12 from strap 20, after which T-portion 61 may be released. After releasing T-portion 61 free from grommet 62, elastic strip 70 constricts to its relaxed and shortened state to draw T-portion 61 into pocket 80 through open end 83 to store and conceal T-portion 61 in pocket 80.

Referencing FIGS. 1, 2, and 8, engagement assembly 60 (referenced only in FIG. 8) formed between outer end 47B of strap 47 of gel pack 12 and strap 21 of brassiere 11 is likewise formed with pouch 80 including material 81 and open end 83, the structure and operation of which is identical to pouch 80 formed in strap 20 in conjunction with engagement assembly 60 formed in strap 20. In FIG. 8, portions of garment 10 are broken away for illustrative purposes illustrating pocket 80 formed in outer surface 21A of strap 21 and engagement assembly 60, including T-portion 61 and gusset 62, formed between strap 21 of brassiere 11 and outer end 47B of strap 47 of gel pack 12 and engaged detachably coupling strap 47 of gel pack 12 to strap 21 of brassiere, in which elastic strip 70 is under no stretching influence and is in its relaxed or retracted state such that T-portion 61 is located in pocket 80.

The invention has been described above with reference to a preferred embodiment. However, those skilled in the art will recognize that changes and modifications may be made to the embodiment without departing from the nature and scope of the invention. Various changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

The invention claimed is:

1. A therapeutic garment, comprising:
a brassiere including opposed first and second shoulder straps formed with opposed first and second breast-receiving cups, respectively, each having an outer surface;
a reusable gel pack for heat or cold therapy suspended from the first and second shoulder straps extending downwardly from the first and second shoulder straps to the first and second breast-receiving cups overlying and extending across the outer surfaces of the first and second breast-receiving cups to provide heat or cold therapy to the first and second breast-receiving cups at the outer surface of each of the first and second breast-receiving cups;
a first inverted pocket formed in the first shoulder strap;
a second inverted pocket formed in the second shoulder strap;
first and second engagement elements formed in the first and second shoulder straps within the first and second inverted pockets, respectively; and
first and second complemental engagement elements formed in the reusable gel pack detachably secured to the first and second engagement elements, respectively, detachably suspending the reusable gel pack from the first and second shoulder straps from within the first and second inverted pockets formed in the first and second shoulder straps, respectively.

2. A therapeutic garment, comprising:
a brassiere including opposed first and second shoulder straps formed with opposed first and second breast-receiving cups, respectively, each having an opposed outer surface;
a reusable gel pack for heat or cold therapy;
first and second engagement elements formed in the first and second shoulder straps, respectively;
first and second complemental engagement elements formed in the reusable gel pack detachably secured to the first and second engagement elements, respectively, detachably suspending the reusable gel pack from the first and second shoulder straps; and
the reusable gel pack extending downwardly from the first and second shoulder straps to the first and second breast-receiving cups overlying and extending across the outer surfaces of the first and second breast-receiving cups to provide heat or cold therapy to the first and second breast-receiving cups at the outer surface of each of the first and second breast-receiving cups.

3. A therapeutic garment according to claim 2, wherein the first engagement element comprises one of a first male engagement element and a first female engagement element, and the first complemental engagement element comprises the other of the first male engagement element and the first female engagement element, and wherein the second engagement element comprises one of a second male engagement element and a second female engagement element, and the second complemental engagement element comprises the other of the second male engagement element and the second female engagement element.

4. A therapeutic garment according to claim 2, further comprising:
a first inverted pocket formed in the first shoulder strap;
the first engagement element formed in the first inverted pocket formed in the first shoulder strap;
a second inverted pocket formed in the second shoulder strap;
the second engagement element formed in the second inverted pocket formed in the second should strap; and
the first engagement element elastically coupled to the first shoulder strap for movement between a first position in the first inverted pocket from in the first shoulder strap and a second position extending outwardly with respect to the first inverted pocket formed in the first shoulder strap toward the breast-receiving cup, and the second engagement element elastically coupled to the second shoulder strap for movement between a first position in the second inverted pocket formed in the second shoulder strap and a second position extending outwardly with respect to the second inverted pocket formed in the shoulder strap toward the second breast-receiving cup.

5. A therapeutic garment, comprising:
a brassiere including opposed first and second shoulder straps formed with opposed first and second breast-receiving cups, respectively, each having an outer surface;
a reusable gel pack for heat or cold therapy formed with opposed first and second connector straps;
first and second engagement elements formed in the first and second shoulder straps, respectively;
first and second complemental engagement elements formed in first and second connector straps, respectively, detachably secured to the first and second engagement elements, respectively, detachably suspending the reusable gel pack from the first and second shoulder straps; and
the first and second connector straps extending downwardly along the first and second shoulder straps, respectively, to the reusable gel pack overlying and extending across the outer surfaces of the first and second breast-receiving cups to provide heat or cold therapy to the first and second breast-receiving cups at the outer surface of each of the first and second breast-receiving cups.

6. A therapeutic garment according to claim 5, wherein the first engagement element comprises one of a first male engagement element and a first female engagement element, and the first complemental engagement element comprises the other of the first male engagement element and the first female engagement element, and wherein the second engagement element comprises one of a second male engagement element and a second female engagement element, and the second complemental engagement element comprises the other of the second male engagement element and the second female engagement element.

7. A therapeutic garment according to claim 5, further comprising:
a first inverted pocket formed in the first shoulder strap;
the first engagement element formed in the first inverted pocket formed in the first shoulder strap;
a second inverted pocket formed in the second shoulder strap; and
the second engagement element formed in the second inverted pocket formed in the second shoulder strap.

8. A therapeutic garment according to claim 7, further comprising the first engagement element elastically coupled to the first shoulder strap for movement between a first position in the first inverted pocket formed in the first shoulder strap and a second position extending outwardly with respect to the first inverted pocket formed in the first shoulder strap toward the first breast-receiving cup; and the second engagement element elastically coupled to the second shoulder strap for movement between a first position in the second inverted pocket formed in the second shoulder strap and a second position extending outwardly with respect to the second inverted pocket formed in the second shoulder strap toward the second breast-receiving cup.

* * * * *